United States Patent [19]

Osei-Gyimah et al.

[11] Patent Number: 5,302,592
[45] Date of Patent: Apr. 12, 1994

[54] USE OF SUBSTITUTED 3-THIOACRYLOYL COMPOUNDS AS ANTIMICROBIAL AGENTS

[75] Inventors: Peter Osei-Gyimah, Horsham, Pa.; Samuel E. Sherba, Willingboro, N.J.; Raj J. Mehta, King of Prussia, Pa.; Barry C. Lange, Lansdale, Pa.; Rhoda W. Joseph, Buckingham, Pa.

[73] Assignee: Rohm and Haas Company, Philadelphia, Pa.

[21] Appl. No.: 107,422

[22] Filed: Aug. 16, 1993

Related U.S. Application Data

[63] Continuation of Ser. No. 880,471, May 6, 1992, abandoned, which is a continuation of Ser. No. 747,157, Aug. 15, 1991, abandoned, which is a continuation-in-part of Ser. No. 568,809, Aug. 18, 1990, abandoned.

[51] Int. Cl.$^5$ ............... A01N 31/02; A01N 43/78
[52] U.S. Cl. .................. 514/230.8; 514/255; 514/345; 514/369; 514/381; 514/400; 514/445; 514/514; 514/520; 514/521; 514/526; 514/527; 514/631; 514/547; 514/549
[58] Field of Search ........... 514/369, 445, 381, 345, 514/400, 230.8, 255, 514, 520, 521, 526, 527, 631, 549, 547

[56] References Cited

U.S. PATENT DOCUMENTS

| | | | |
|---|---|---|---|
| 2,469,317 | 5/1949 | Shokal | 514/549 |
| 3,148,109 | 9/1964 | Miller | 514/547 |
| 3,914,301 | 10/1975 | Miller et al. | 558/170 |
| 4,115,103 | 9/1978 | Sugimura et al. | 71/98 |
| 4,123,254 | 10/1978 | Iwasaki et al. | 71/98 |
| 4,169,850 | 10/1979 | Miyamoto et al. | 564/204 |
| 4,174,339 | 11/1979 | Matsuda et al. | 564/204 |
| 4,198,304 | 4/1980 | Inoue et al. | 564/204 |
| 4,612,049 | 9/1986 | Bernei et al. | 548/165 |
| 5,118,681 | 6/1992 | Amick et al. | 544/158 |
| 5,166,390 | 11/1992 | Weinstein et al. | 558/254 |
| 5,224,980 | 7/1993 | Austin et al. | 514/231.8 |

FOREIGN PATENT DOCUMENTS

| | | |
|---|---|---|
| 2536252 | 2/1977 | Fed. Rep. of Germany . |
| 2821639 | 11/1979 | Fed. Rep. of Germany . |
| 2014428 | 4/1970 | France . |
| 36622 | 4/1975 | Japan . |

OTHER PUBLICATIONS

Hedegaard et al., *Tetrahedron*, vol. 27, pp. 3853-3859 (1971).
Chemical Abstracts vol. 94, No. 11, Abstract 78267 (Mar. 1981).
Tetrahedron, 41(1), 801 (1985), M. Giffard, J. Cousseau & L. Gouin.
Justus Liebigs, Annalen der Chemie, 8, 1249 (1977).
J. Amer Chem Soc, 101 (21) 6306 (1979).
(CA61:11954a), 1964 only abstract considered.
J. Org. Chem, 30, 2660-2665 (1965).
Bulletin of the Chemical Society of Japan, Ando T. Shioi S., Nakagawa M. (1972) 45, 2611.
G. F. Dvorko, N. M. Soboleva, and T. F. Karpenko, (1969); (CA70:96122k). only abstract was considered.
H. F. Plaenler, J. Costell, R. B. Woodward, Journal of the American Chemical Society, 101(21), 6306 (1979).
W. Chodkiewicz, CA (1958:#14565c).

Primary Examiner—Joseph Paul Brust
Assistant Examiner—Mary Susan H. Gabilan
Attorney, Agent, or Firm—Michael B. Fein

[57] ABSTRACT

Use as microbicides of thioacryloyl compounds of the formula

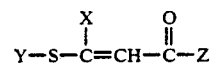

Compounds and compositions are also disclosed.

6 Claims, No Drawings

USE OF SUBSTITUTED 3-THIOACRYLOYL COMPOUNDS AS ANTIMICROBIAL AGENTS

This application is a continuation of application Ser. No. 880,471, filed May 6, 1992, now abandoned, which is a continuation of application Ser. No. 747,157, filed Aug. 15, 1991, which now abandoned, which continuation in part of Ser. No. 07/568,809 filed Aug. 18, 1990, now abandoned.

BACKGROUND OF THE INVENTION

1. Field of the Invention

This invention relates to the field of antimicrobial agents.

2. Description of the Prior Art

Certain classes of thioacrylates and thioacrylamides have been prepared as antimicrobials but no compound within those classes has achieved commercial success.

U.S. Pat. Nos. 4,115,103; 4,123,254; 4,169,850; and 4,198,304 to Kao Soap Co., disclose alkyl substituted beta-thioacrylamides and beta-thioacrylic acids (and salts thereof) and the corresponding alkyl sulfone and alkyl sulfoxide derivatives as germicidal herbicides, antibiotics, and as antimicrobial agents in non-food or medicinal compositions.

German patent DE 2536252 to Bayer AG discloses beta-thiocyanovinyl aryl ketones as antimicrobial agents. Thioalkyl-and thiocyano-alkyl- alpha-substituted acrylic acids (and esters thereof) are disclosed as plant growth regulators in Japanese Kokai J 50-03622 to Mitsubishi Chemical. German unexamined patent application 2821639 to Hoechst AG discloses S-substitutedalkyl-beta-thioacryloyl compounds as fungicides and bactericides.

Methyl 3-thiocyanoacrylate and dimethyl alpha-thiocyanofumarate are known compounds (*Tetrahedron*, 41(4), 801 (1985)), but have not been disclosed as antimicrobial compounds. Cis-3-thiocyanoacrylic acid is a known compound (*Justus Liebigs Annalen der Chemie*, 8, 1249 (1977)) but has not been disclosed as an antimicrobial compound. Beta-carbomethoxyvinylisothiurium chloride is a known compound. (*J. Amer. Chem. Soc.*, 101(21), 6306 (1979)) but has not been disclosed as an antimicrobial compound. Methyl 3-thio(propan-2-on-1-yl)acrylate is a known compound (*Berichte*, 97(8), 2109-17 (1964)) but has not been disclosed as an antimicrobial compound. N,N-Dimethyl-3-thiocyanoacrylamide is a known compound (*J. Org. Chem.*, 30, 2660-2665 (1965)) but has not been disclosed as an antimicrobial compound.

SUMMARY OF THE INVENTION

Many of the antimicrobials of the prior art have toxicity and/or environmental problems.

It is an object of the present invention to provide novel antimicrobial compounds which have improved toxicity profiles and are not harmful to the environment.

These objects, and others which will become apparent from the following disclosure, are achieved by the present invention which comprises the use as a microbicide of an effective amount of a thioacryloyl compound of the formula

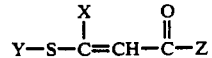

wherein

Z is selected from the group consisting of OR, R and $NR^1R^2$;

R is selected from the group consisting of hydrogen; $(C_1-C_{18})$alkyl; $(C_2-C_8)$alkenyl; $(C_2-C_8)$haloalkynyl; 2-(5-chlorothienyl)methyl; phenyl optionally substituted with one or more substituents selected from the group consisting of halo-, $(C_1-C_3)$alkoxy-, nitro-, and $(C_1-C_3)$alkyl; phenacyl optionally substituted with one or more substituents selected from the group consisting of ring halo-, $(C_1-C_3)$alkoxy-, nitro-, and $(C_1-C_3)$alkyl; arylakyl optionally substituted with one or more substituents selected from the group consisting of ring halo-, $(C_1-C_3)$alkoxy-, nitro-, and $(C_1-C_3)$alkyl;

$R^1$ and $R^2$ are independently selected from $(C_1-C_8)$alkyl and phenyl, or $R^1$ and $R^2$ may be joined together with the nitrogen atom to which they are attached to form a ring containing 4 to 5 carbon atoms with or without an oxygen heteroatom;

X is selected from the group consisting of hydrogen, halogen, phenyl, $CO_2CH_3$, and $(C_1-C_3)$alkyl; and Y is selected from the group consisting of CN, $CH(COCH_3)_2$, $CH_2COCH_3$, $CH_2CN$, $CH_2CO_2C_2H_5$, propargyl, $SCH=CHCO_2CH_3$, $C(=NH)NH_2$ hydrochloride, 2-(5-chlorothienyl)methyl, and a saturated or unsaturated heterocyclic 5- or 6-membered ring with 1 to 4 heteroatoms selected from the group consisting of S, O, or N, said ring being unsubstituted or substituted with substituents independently selected from the group consisting of unsubstituted or halosubstituted alkyl of 1 to 8 carbon atoms, unsubstituted or halosubstituted alkenyl or alkynyl of 2 to 8 carbon atoms, nitro, cyano, halo, $(C_1-C_8)$alkoxy, amino, alkylamino, dialkylamino, and benzyl; or optionally fused to a benzene ring which is optionally substituted with substituents independently selected from the group consisting of unsubstituted or halosubstituted alkyl of 1 to 8 carbon atoms, unsubstituted or halosubstituted alkenyl or alkynyl of 2 to 8 carbon atoms, nitro, cyano, halo, $(C_1-C_8)$alkoxy, amino, alkylamino, and dialkylamino; or said nitrogens in the nitrogen-containing heterocycles possibly being N-oxides;

provided that when Y is heterocyclic and Z is R, R is $(C_1-C_{18})$alkyl;

provided that when Z is $NR^1R^2$, Y is CN; and provided that when Z is R, X is hydrogen, and Y is CN, R is not substituted or unsubstituted phenyl; substituted or unsubstituted phenacyl; or substituted or unsubstituted arylalkyl.

The invention also comprises the aforementioned thioacryloyl compounds except compounds wherein (a) X is hydrogen, Y is CN and Z is hydrogen, methoxy or dimethylamino;

(b) X is hydrogen, Z is methoxy and Y is $CH_2COCH_3$ or $C(=NH)NH_2$ hydrochloride; and (c) X is $CO_2CH_3$, Y is CN and Z is methoxy.

A preferred aspect of the invention comprises the use of methyl cis-3-thiocyanoacrylate, iodopropargyl cis-3-thiocyanoacrylate, methyl trans-3-thiocyanoacrylate, and cis-4-thiocyano-3-buten-2-one at concentrations from about 5 to about 300 ppm in compositions for controlling microorganisms in cooling tower water and paper mill systems.

DETAILED DESCRIPTION OF THE INVENTION AND THE PREFERRED EMBODIMENTS

The compounds of the invention have been discovered to be unexpectedly effective antimicrobials.

Some representative compounds include the following:

1. Methyl cis-3-thiocyanoacrylate
2. Cis-3-thiocyanoacrylic acid
3. Ethyl cis-3-thiocyanoacrylate
4. n-Butyl cis-3-thiocyanoacrylate
5. Phenyl cis-3-thiocyanoacrylate
6. Iodopropargyl cis-3-thiocyanoacrylate
7. Dimethyl alpha-thiocyanofumarate
8. 2,5-Dinitrobenzyl cis-3-thiocyanoacrylate
9. 5-Chloro-thien-2-yl-methyl cis-3-thiocyanoacrylate
10. Benzyl cis-3-thiocyanoacrylate
11. 4-Chlorobenzyl cis-3-thiocyanoacrylate
12. p-Chloroacetophenyl cis-3-thiocyanoacrylate
13. 3-Methoxybenzyl cis-3-thiocyanoacrylate
14. 2,5-Dichlorobenzyl cis-3-thiocyanoacrylate
15. Cis-beta-carbomethoxyvinylisothiouronium chloride
16. Methyl cis-3-thio(1-acetylpropan-2-on-1-yl)acrylate
17. Methyl cis-3-thio(propan-2-on-1-yl)acrylate
18. Bis-cis-(carbomethoxyvinyl)disulfide
19. Methyl trans-3-thiocyanoacrylate
20. Methyl cis-3-propargylthioacrylate
21. Methyl cis-3-(5-chlorothien-2-yl-methyl)acrylate
22. Methyl 3-bromo-3-thiocyanoacrylate
23. N,N-Dimethyl cis-3-thiocyanoacrylamide
24. N-(cis-3-thiocyanoacryloyl)piperidine
25. N-(cis-3-thiocyanoacryloyl)morpholine
26. N-Methyl-N-n-butyl cis-3-thiocyanoacrylamide
27. N-Methyl-N-phenyl cis-3-thiocyanoacrylamide
28. Cis-4-thiocyano-3-buten-2-one
29. Methyl cis-3-(cyanomethylthio)acrylate
30. Methyl cis-3-(ethylcarboxymethylthio)acrylate
31. Cis-5-thiocyano-4-penten-3-one
32. Cis-8-thiocyano-7-octen-6-one
33. 4-Phenyl-4-thiocyano-3-buten-2-one
34. 4-(2-Mercaptobenzothiazolyl)-3-buten-2-one
35. Cis-4-(5-mercapto-1-methyltetrazoyl)-3-buten-2-one
36. Cis-4-(2-mercaptothiazolinyl)-3-buten-2-one
37. Trans-4-(2-mercaptothiazolinyl)-3-buten-2-one
38. Cis-4-(2-mercaptopyridinyl)-3-buten-2-one
39. Trans-4-(2-mercaptopyridinyl)-3-buten-2-one
40. Cis-4-(2-mercaptopyridinyl-N-oxide)-3-buten-2-one
41. Cis-4-(2-mercaptothiazolyl)-3-buten-2-one
42. Trans-4-(2-mercaptothiazolyl)-3-buten-2-one
43. 1-Mercaptoimidazolyl-3-buten-2-one
44. Cis-4-(2-mercapto-1-methylimidazolyl)-3-buten-2-one
45. 4-(2-Mercapto-1-methylimidazolyl)-3-buten-2-one

TABLE 1

Structures and Physical Data of Representative Compounds of Formula I, Z = OR

| Comp. No. | R | X | Y | Melting or Boiling Point |
|---|---|---|---|---|
| 1 | $CH_3$ | H | CN | 69–70° C. |
| 2 | H | H | CN | 161–166° C. |
| 3 | $CH_2CH_3$ | H | CN | 72° C./0.5 mm |
| 4 | $CH_2CH_2CH_2CH_3$ | H | CN | 85° C./0.3 mm |
| 5 | Ph | H | CN | 79–83° C. |
| 6 | $CH_2C{\equiv}C{-}I$ | H | CN | 141–143.2° C. |
| 7 | $CH_3$ | $COOCH_3$ | CN | 32–35° C. |
| 8 | $CH_2Ph(2,5{-}di{-}NO_2)$ | H | CN | 138–140° C. |
| 9 | $CH_2(5{-}Cl{-}Thien{-}2{-}yl)$ | H | CN | 57–59.5° C. |
| 10 | $CH_2Ph$ | H | CN | 48.5–50.5° C. |
| 11 | $CH_2Ph(4{-}Cl)$ | H | CN | 69–70° C. |
| 12 | $CH_2COPh(4{-}Cl)$ | H | CN | 127–129° C. |
| 13 | $CH_2Ph(3{-}OCH_3)$ | H | CN | 64–66° C. |
| 14 | $CH_2Ph(2,5{-}di{-}Cl)$ | H | CN | 135–138° C. |
| 15 | $CH_3$ | H | C(=NH)NH$_2$ (hydrochloride salt) | 166–167° C. |
| 16 | $CH_3$ | H | $CH(COCH_3)_2$ | 61–64° C. |
| 17 | $CH_3$ | H | $CH_2COCH_3$ | 76–79° C. |
| 18 | $CH_3$ | H | $S{-}CH{=}CH{-}COOCH_3$ | 133–136° C. |
| 19 | $CH_3$ | H | CN | 70° C./0.3 mm |
| 20 | $CH_3$ | H | $CH_2C{\equiv}C{-}H$ | 85° C./0.25 mm |
| 21 | $CH_3$ | H | 5-Cl-Thiophene-2-methylene | 49.5–52° C. |
| 22 | $CH_3$ | Br | CN | 139–142.5° C. |
| 29 | $CH_3$ | H | $CH_2CN$ | 63–66° C. |
| 30 | $CH_3$ | H | $CH_2CO_2C_2H_5$ | Oil |

TABLE 2

Structures and Physical Data of Representative Compounds of Formula I, Z = $NR^1R^2$, X = H, Y = CN

| Comp. No. | $R^1$ | $R^2$ | Melting Point (°C.) |
|---|---|---|---|
| 23 | $CH_3$ | $CH_3$ | 99–102 |
| 24 | —$CH_2CH_2CH_2CH_2CH_2$— | | 88–90 |
| 25 | —$CH_2CH_2OCH_2CH_2$— | | 89–91.5 |
| 26 | $CH_3$ | n-Bu | Oil |
| 27 | $CH_3$ | Ph | 60–62 |

TABLE 2A

Structure and Physical Data of Representative Compounds of Formula I, Z = R, Y = CN

| Comp. No. | R | X | Melting Point (°C.) |
|---|---|---|---|
| 28 | $CH_3$ | H | 44–46 |
| 31 | $CH_2CH_3$ | H | Oil |
| 32 | $CH_2CH_2CH_2CH_2CH_3$ | H | Oil |
| 33 | $CH_3$ | Ph | Oil |

TABLE 2B

Structure and Physical Data of Representative Compounds of Formula I, Z = CH₃, X = H

| Comp. No. | Y | Melting Point (°C.) |
|---|---|---|
| 34 | benzothiazol-2-yl | 85–88.5 |
| 35 | 1-methyl-1H-tetrazol-5-yl | 112–114 |
| 36(cis) | thiazolidin-2-yl | 69–72 |
| 37(trans) | thiazolidin-2-yl | Oil |
| 38(cis) | pyridin-2-yl | 57–58.5 |
| 39(trans) | pyridin-2-yl | Oil |
| 40 | pyridin-2-yl N-oxide | 139–143.5 |
| 41(cis) | thiazol-2-yl | 43.5–45.5 |
| 42(trans) | thiazol-2-yl | Oil |
| 43(cis and trans) | 1H-imidazol-2-yl | 117–120 |
| 44(cis) | 1-methyl-imidazol-2-yl | Oil |
| 45(cis and trans) | 1-methyl-imidazol-2-yl | Oil |

The compounds of Formula I, where Z=OR; R=alkyl, phenyl and substituted phenyl, arylalkyl and substituted arylalkyl; X=H; and Y=CN, can be prepared by the esterification of cis-3-thiocyanoacrylic acid, Compound 2, as follows:

NC—S—CH=CH—COOH 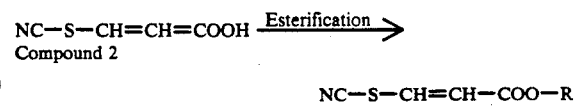
Compound 2

NC—S—CH=CH—COO—R

Various esterification methods known in the literature may be used to prepare the compounds. Two useful procedures are described here. A suspension of compound 2 in anhydrous solvents such as acetonitrile, dioxane or toluene is treated with 1,8-diazabicyclo-(5.4.0)undec-7-ene, (DBU), at temperatures ranging from 0°–25° C. The resulting solution is allowed to react with commercially available alkyl, arylalkyl, and substituted arylalkyl halides (Aldrich Chemical Company) at temperatures ranging from 0°–25° C. The reaction generally takes place within 1–24 hours. Alternatively, compound 2 may be converted to the mixed anhydride and then treated with alcohols or phenols to give the esters. Thus, compound 2 may be suspended in dry solvents such as toluene, acetonitrile, or dioxane and treated with triethylamine at temperatures ranging from 0°–25° C. The resulting solution is treated with ethyl chloroformate or methane sulfonyl chloride at 0°–25° C. The resulting mixed anhydride is allowed to react with commercially available alcohols or phenols at temperatures ranging from 0°–25° C. The reaction usually takes place within 1 to 24 hours.

Iodopropargyl alcohol is prepared by a published procedure (Bulletin of the Chemical Society of Japan, Ando, T.; Shioi, S.; Nakagawa, M., (1972), 45,2611).

Cis-3-thiocyanoacrylic acid, compound 2, which serves as the starting material for esterification into many of the compounds of Structure I, is known in the literature (G. Simchen and G. Entenmann, Justus Liebigs Annalen der Chemie, No. 8, 1249 (1977)). The compound is prepared by treating commercial propiolic acid with sodium or ammonium thiocyanate in aqueous sulfuric acid solution at 0° C. and then allowing the mixture to warm to room temperature to precipitate the compound.

The chemistry of the thiocyano group and its addition to triple bonds are discussed in the text: "The Chemistry of Cyanates and their Thio Derivatives", parts 1 and 2, (Ed. S. Patai), Wiley and Sons, (1977).

Methyl cis-3-thiocyanoacrylate, compound 1, is cited in the following literature:

1. M. Giffard, J. Cousseau and L. Gouin, Tetrahedron, 41(4), 801 (1985).
2. G. F. Dvorko, N. M. Soboleva, and T. F. Karpenko, Dokl, Acad. SSSR, 184(45), 850 (1969); (CA70:96122k).

The compound is readily prepared by treating commercial methyl propiolate with ammonium thiocyanate in aqueous sulfuric acid solution at 0° C. and then allowing the mixture to warm up to room temperature to precipitate the compound.

A useful procedure for preparing the S-substituted compounds of Formula I,Z=OCH₃, X=H, and Y=CH(COCH₃)₂, CH₂CN, CH₂CO₂C₂H₅, CH₂COCH₃, alkynyl, and arylalkyl (Compounds 16, 17, 20, 21, 29 and 30) starts with cis-beta-carbomethoxyvinylisothiouronium chloride, Compound 15, which is prepared and hydrolyzed to the mercaptide according to literature procedure: H. R. Pfaendler, J. Costell, and R. B. Woodward, *Journal of the American Chemical Society*, 101(21), 6306(1979). The mercaptide, which is not isolated, is treated with commercially available halides of Y at temperatures ranging from −10° to 25° C. in aqueous ethanol solution as shown below. The reaction usually takes place within 1–24 hours.

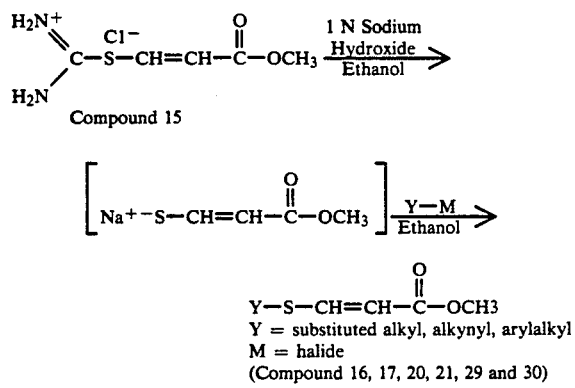

Compound 15

$$\left[ Na^+ {}^-S-CH=CH-\overset{O}{\underset{\|}{C}}-OCH_3 \right] \xrightarrow[\text{Ethanol}]{Y-M}$$

$$Y-S-CH=CH-\overset{O}{\underset{\|}{C}}-OCH_3$$

Y = substituted alkyl, alkynyl, arylalkyl
M = halide
(Compound 16, 17, 20, 21, 29 and 30)

Methyl trans-3-thiocyanoacrylate, compound 19, is prepared from commercially available trans-3-chloroacrylic acid (Aldrich Chemical Company) as follows: An aqueous hydrochloric or sulfuric acid solution of ammonium thiocyanate is treated with trans-3-chloroacrylic acid methanol at temperatures ranging from 25°–50° C. The mixture is then heated to reflux for a period of 1 to 24 hours. The mixture is extracted with chloroform which is washed with aqueous sodium bicarbonate solution. Compound 19 is obtained upon evaporation of the solvent.

Methyl 3-bromo-3-thiocyanoacrylate, compound 22, is prepared by allowing methyl bromopropiolate to react with ammonium thiocyanate in sulfuric acid solution at temperatures ranging from 0°–25° C. The reaction takes place in 1 to 5 hours. The starting material, methyl bromopropiolate, can be prepared according to a published procedure: W. Chodkiewicz, *Ann. Chim.* (Paris), 2(13), 819 (1957).

Cis-beta-thiocyanovinyl ketones, e.g., compounds 28, 31, 32 and 33, are prepared by allowing acetylenic ketones to react with ammonium thiocyanate in sulfuric acid solution at temperatures ranging from 0°–25° C. The reaction takes place in 1 to 2 hours.

Cis-4-(5-mercapto-1-methyltetrazolyl-3-buten-2-one, compound 35, is prepared by allowing 5-mercapto-1-methyltetrazole sodium salt hydrate to react with cis-4-thiocyano-3-buten-2-one (compound 28, prepared as above) in aqueous ethanol at 25° C. The reaction takes place in 18 hours.

Cis- and trans-4-(2-mercatothiazolinyl)-3-buten-2-one, compounds 36 and 37, are prepared by allowing 2-mercaptothiazoline to react with 3-butyn-2-one in aqueous ethanol at temperatures ranging from 25° C. to reflex. The reaction takes place in 20 hours.

As stated above, compositions comprising a compound according to formula I and either an agronomically acceptable carrier, a cosmetic agent, a cutting oil, a soap or synthetic detergent, a stabilizer, a film forming material, or the like have a wide range of utility for protecting against or controlling microorganisms from a wide variety of classes including fungus, bacteria, algae, viruses and yeasts. The preferred utilities of the compositions are to protect wood, paint, adhesive, glue, paper, pulp/paper slurries, textile, leather, plastics, cardboard, lubricants, cosmetics, food, caulking, feed and industrial cooling water from microorganisms.

Especially preferred compounds are methyl cis-3-thiocyanoacrylate, iodopropargyl cis-3-thiocyanoacrylate, methyl trans-3-thiocyanoacrylate, and cis-4-thiocyano-3-buten-2-one. Preferred concentrations are about 5 to about 300 ppm based on weight of material being protected. Preferred applications for controlling microorganisms are in industrial cooling water and paper mill systems. For example, especially preferred is using the compounds at about 5–125 ppm in cooling tower water systems and at 15–250 ppm in pulp and paper slurries.

The following lists specific industries and applications of the compounds and compositions.

| Industry | Application |
|---|---|
| Adhesives, sealants | adhesives |
| | caulks |
| | sealants |
| Agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated consumer & industrial products | air fresheners |
| | fabric softeners |
| | hand cleaners |
| | polishes, floor, furniture, shoe |
| | sponges & towelettes |
| | spray starch |
| | waxes |
| Industrial processing, misc | dry cleaning fluids preservation |
| | electrodeposition paint, baths, rinses |
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| Laundry | household laundry products |
| | laundered goods |
| | laundry rinse water |
| | pre-washers |

| Industry | Application |
|---|---|
| | sanitizers-laundry |
| | removers, spot & stain |
| Leather, leather products | leather and hide |
| | leather and hide products |
| Lubricants, hydraulic aids | automotive lubricants and fluids |
| | conveyor lubricants |
| | greases |
| | hydraulic fluids |
| | hydraulic oils |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings | coating emulsions |
| | paints |
| Paper and wood pulp, their products | absorbant materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products, storage, transportation and production |
| | recycled petroleum products |
| | residual fuel oils |
| | turbine oils |
| Photographic chemicals and process | photographic processing - wash water, rinses |
| | photoplate processing chemicals (developers, stabilizers etc) |
| Printing | fountain solutions (printing) |
| | ink components (pigments, resins, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers- food processing |
| | sanitizers-medical |
| | sanitizers-rendering |
| | sanitizers-veterinary |
| Soaps, detergents, cleaners | cleaners |
| | detergents, hand automatic laundry, other |
| | household cleaners |
| | industrial cleaners |
| | liquid soaps, hand, dish, laundry |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electonic circuitry |
| | electonics chemicals |
| | enzymes-food production |
| | enzymes-industrial |
| | gel cushions |
| | laboratory reagents |
| | marine antifoulants |
| | mildewcides |
| | mining applications |
| | natural rubber latex |
| | oil field applications |
| | pipes |
| | plastics |
| | polymer sytems |
| | polymers and resins (synthetic and natural) |
| | reagent preservation |
| | rubber |
| | rubber products |
| | skin remover |
| | solid protective/decorative |

| Industry | Application |
|---|---|
| | films |
| | swimming pools |
| | waste treatment |
| | water beds |

The amounts of the compound to be used depend on the application. The useful amounts for a particular application are similar to amounts used for other microbicidal compounds.

The compound can be used in combination with other microbicides. The term "microbicide" is considered equivalent to "antimicrobial" as used herein.

Suitable methods of application of compounds of formula I to control fungi, bacteria, algae, viruses, yeasts, and the like are in amounts and with carriers, etc., as are well known in the art.

The following examples are presented to illustrate a few embodiments of the invention, but are not to be considered as limiting.

EXAMPLE 1

Phenyl cis-3-Thiocyanoacrylate (Compound 5)

Triethylamine (2.3 g., 0.031 mole) in 5 ml of dry toluene was added dropwise to a stirred suspension of compound 2 (4.0 g., 0.031 mole) in 30 ml of dry toluene at 0° C. To the resulting solution, methanesulfonyl chloride (3.55 g., 0.031 mole) in 15 ml of dry toluene was added dropwise at 0° C. and stirred for 30 minutes. A solution of phenol (2.9 g., 0.031 mole) and dimethylaminopyridine (DMAP) (3.5 g., 0.028 mole) in 40 ml of dry toluene was added dropwise with stirring at 0° C. The mixture was allowed to warm to room temperature and stirred for an additional 3 hours. The mixture, consisting of yellowish gum in a two-phase mixture with toluene, was diluted with methylene chloride, poured into water and the organic phase was separated. The aqueous phase was extracted with methylene chloride. The combined organic phase was washed with sodium bicarbonate solution, water, dried (MgSO$_4$) and concentrated. The residue was column-chromatographed on silica gel using hexane/ether (4:1) as eluant to give product as white crystals, 2.9 g: mp 79°-83° C.; IR (KBr) 1700, 2175 cm$^{-1}$.

EXAMPLE 2

Benzyl cis-3-Thiocyanoacrylate (Compound 10)

To a stirred suspension of compound 2 (3.0 g., 0.023 mole) in dry acetonitrile (40 ml), a solution of DBU (3.54 g., 0.023 mole) in 10 ml of dry acetonitrile was added dropwise, keeping the temperature of the mixture below 25° C. To the resulting solution was added dropwise a solution of benzyl bromide (4.0 g., 0.023 mole) in 15 ml of dry acetonitrile at room temperature. After stirring for 5 hours, the mixture was poured into water, and extracted with ether. The ether extract was washed with water, dried (MgSO$_4$) and concentrated to give an oil which solidified upon standing, 4.3 g. The solid recrystallized from ethanol/hexane mixture as plate-like crystals: mp 48.5°-50.5° C.; IR (KBr) 1695, 2180 cm.$^{-1}$.

EXAMPLE 3

Methyl cis-3-Thio(1-acetylpropan-2-on-1-yl) acrylate (Compound 16)

To a stirred solution of cis-beta-carbomethyoxyvinylisothiouronium chloride (compound 15) (3.92 g., 0.02 mole) in 80 ml of 95% ethanol, a pre-cooled solution of sodium hydroxide (1N, 40 ml, 0.04 mole) was added within 5 minutes at −10° C. To the white precipitate which formed immediately, consisting of sodium cis-beta-carbomethyoxyvinylmercaptide, urea and sodium chloride, was added a solution of 3-chloro-2,4-pentanedione (2.68 g., 0.02 mole) in 30 ml of 95% ethanol at −10° C. After allowing the mixture to warm to room temperature, it was stirred for an additional 5 hours and then poured into water, followed by extraction with chloroform. The chloroform extract was washed with water, dried (MgSO$_4$), and concentrated. The residual oil was purified by column chromatography using hexane/ether (2:3) as eluant. The resulting oil, 2.1 g, solidified on standing and was recrystallized from ethanol/hexane mixture: mp 61°-64° C.; NMR (CDCl$_3$) 17.1 (s, 1H); 6.8 (d, 1H, J=9.3 cps); 5.95 (d, 1H, J=9.3 cps); 3.8 (s, 3H); 2.35 (s, 6H).

EXAMPLE 4

Methyl trans-3-Thiocyanoacrylate (Compound 19)

To a stirred solution of ammonium thiocyanate (7.2 g., 0.095 mole) in 4N sulfuric acid solution (50 ml) at 40° C., a solution of trans-3-chloroacrylic acid (10.0 g., 0.095 mole) in 35 ml of methanol was added dropwise within 5 minutes. The mixture was refluxed for 18 hours, cooled and poured into water which was extracted thoroughly with ether. The ether extract was washed with saturated sodium bicarbonate solution and then with water. After drying (MgSO$_4$), the solution was concentrated to give an oil which distilled at 70° C./0.3 mm; yield, 7.2 g.;

NMR (CDCl$_3$) 7.3 (d, 1H, J=14.4 cps); 6.35 (d, 1H, J=14.4 cps); 3.8 (s, 3H);

IR(KBr) 2180, 1725 cm$^{-1}$.

EXAMPLE 5

Methyl 3-Bromo-3-Thiocyanoacrylate (Compound 22)

To a stirred solution of ammonium thiocyanate (3.06 g., 0.04 mole) in 2M aqueous sulfuric acid (20 ml) at 0° C., methyl 3-bromopropiolate (3.26 g., 0.02 mole) was added dropwise, neat, over 5 minutes. After keeping the temperature at 0° C. for 1 hour, the mixture, consisting of a solid precipitate in the aqueous solution, was extracted with ether which was washed with water, dried (MgSO$_4$), and concentrated. The residual solid was suspended in hexane and removed by filtration, yielding 2.4 g. of product. The solid recrystallized from ethanol as yellowish microcrystals; mp 139°-142.5° C.;

IR (KBr) 2170, 1680 cm$^{-1}$.

EXAMPLE 6

N-(cis-3-Thiocyanoacryloyl)piperidine (Compound 24)

To a stirred suspension of compound 2 (3.06 g., 0.023 mole) in 60 ml of dry toluene, triethylamine (2.35 g., 0.023 mole) in 10 ml of dry toluene was added dropwise, keeping the temperature of the mixture at 0°-5° C. To the resulting solution was added dropwise, ethyl chloroformate (2.53 g., 0.023 mole) in 15 ml of dry toluene at 0°-5° C. After stirring the mixture for 15 minutes, piperidine (2.0 g., 0.023 mole) in 15 ml of dry toluene was added dropwise at 0°-5° C. The mixture was allowed to warm to room temperature, stirred for an additional 2 hours and filtered. The filtrate was washed with water, dried (MgSO$_4$) and concentrated to give an oil which solidified, 2.6 g. The solid was recrystallized from ethanol: mp 88°-90° C.; IR (KBr) 2175, 1630 cm$^{-1}$

EXAMPLE 7

Cis-4-Thiocyano-3-buten-2-one (Compound 28)

To a stirred solution of ammonium thiocyanate (7.6 g., 0.1 mole) in 2M sulfuric acid solution (50 ml) at 0° C., 1-butyn-3-one (3.4 g., 0.05 mole) was added neat over 5 minutes. The resulting solid suspension was stirred at 0° C. for 15 minutes and then allowed to warm to room temperature and then stirred for an additional hour. The solid was removed by filtration and washed with water. After drying, the brown solid was purified by column chromatography on silica gel using hexane/ether (1:4) as eluant. The resulting solid, 3.6 g recrystallized from hexane/ethanol mixture as needles upon standing in the refrigerator: mp 44°-46° C.; IR (KBr) 2150, 1665 cm$^{-1}$.

EXAMPLE 7A

Cis-4-(5-mercapto-1-methyltetrazolyl)-3-buten-2-one (Compound 35)

To a stirred solution of 5-mercapto-1-methyltetrazole sodium salt hydrate (1.1 g., 0.008 mole) in aqueous ethanol (15 ml), a solution of cis-4-thiocyano-3-buten-2-one (Compound 28) in ethanol was added dropwise over 5 minutes. A solid suspension was observed forming over the next 2 hours which was stirred at 25° C. for 18 hours. The volatiles were removed in vacuo and the residue was extracted into ethyl acetate and washed thoroughly with water. After drying (MgSO$_4$), the solution was concentrated. The solid residue was purified via column chromatography on silica gel using hexanes/ethyl acetate (3:2) as eluant to yield 1.1 g of a white solid, mp 112°-114° C. IR (nujol) $u_{c=o}$ 1660 cm$-1$.

EXAMPLE 7B

Cis and trans-4-(2-mercaptothiazolinyl)-3-buten-2-one (Coumpounds 36 and 37)

To a stirred solution of 2-mercaptothiazoline (3.7 g., 0.03 mole) in aqueous ethanol (35 ml) at 35° C., a solution of 3-butyn-2-one (2.0 g., 0.03 mole) in ethanol (10 ml) was added dropwise over 10 minutes. The resulting solution was refluxed for 2 hours and stirred at ambient temperature for 18 hours. The volatiles were removed in vacuo and the residue was extracted into ethyl acetate and washed thoroughly with water. After drying (MgSO$_4$), the solution was concentrated to an amber oil consisting of the cis and trans isomers. Purification and isolation of the isomers was accomplished via column chromatography on silica gel using hexanes/ethyl acetate (4:1), yielding 2.7 g cis-isomer as a white solid, mp 69°-72° C. IR.(nujol) $u_{c=o}$ 1660 cm$-1$. The trans-isomer was recovered as an amber oil, 0.2 g IR (neat) $u_{c=o}$ 1660 cm$-1$.

EXAMPLE 8

Biological Activity

A. Biocidal Activity:

Biocidal evaluations (bactericidal, algicidal, and fungicidal) were carried out.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm (or 100, 50, 25, 12.5, 6.2, 3.1, 1.6, and 0.8), respectively.

Each vessel is then inoculated with a cell suspension of the appropriate test organism. Bacteria are grown in broth, fungi on agar slants for a time and at a temperature appropriate to the species being tested, and algae are a mixture of green algae and blue-green bacteria grown in a nutrient media. At the end of the growth period, in the case of bacteria, the broth is vortexed to disperse the cells.

In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound.

The algae culture contains green algae and blue-green bacteria, and is obtained from a cooling tower in Spring House, Pa. The algae culture is grown in Allen's medium on a rotary shaker under fluorescent room lighting. This culture is further diluted with Allen's medium and then added to the test vessel.

The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:

BACTERIA:
*Pseudomonas fluorescens* (PSFL), gram negative
*Pseudomonas aerugenosa* (PSAE), gram negative
*Escherichia coli* (ECOL), gram negative
*Staphylococcus aureus* (SAUR), gram positive
FUNGI:
*Aspergillus niger* (ANIG)
*Aureobasidium pullulans* (APUL)

The results of the minimum inhibitory concentration (MIC) and SOK tests of compounds of this invention are shown in Table 3 against the microorganism shown in Table 6.

B. In-Vitro Plant Fungicidal Tests:
In-vitro tests of plant diseases were carried out.
The organisms employed in the test are:
PYU *Pythium ultimum* (Oomycete)
PHY *Phytophthora capsici* (Oomycete)
PIR *Piricularia oryzae* (Ascomycete)
HEL *Cochliobolus sativus* (Ascomycete)
BOC *Botrytis cinerea* (Ascomycete)
FUS *Fusarium roseum* (Ascomycete)
SEP *Septoria nodorum* (Ascomycete)
RHI *Rhizoctonia solani* (Basidiomycete)
XAN *Xanthomonas compestris* (bacterium)
Methods:

1. Culture maintenance: Transfers in steps 1 and 2 are done in a laminar flow hood. All 8 fungi and the bacterium used in this test are transferred and maintained on potato dextrose agar plates each week (2 plates/organism). Organisms are used when they are the following ages: a. 1 week old: PYU, PHY, RHI; b. 2 weeks old: XAN, PIR, BOC, HEL, FUS, SEP. *Pythium ultimum* and *Phytophthora capsici* are transferred to asparagine-sucrose broth shake culture (ASB). *Rhizoctonia solani, Fusarium roseum*, and *Xanthomonas campestris* are mainted in yeast extract-dextrose broth (YDB) on a shaker. Culture flasks are inoculated with 6 mycelial plugs each (except for Pythium which is inoculated with only 3 plugs) taken from PDA plates. All liquid shaker cultrues are used after 2 days growth.

2. Inoculum preparation. Conidia and mycelium from PIR, BOC, HEL, and SEP are lightly scraped off into YDB so that mostly conidia are used as inoculum. The conidial suspension is strained through a double layer of cheesecloth to remove mycelial clumps. One plate produces enough conidia or mycelium to inoculate 100 ml of YDB. XAN broth culture is poured (1 ml culture/100 ml broth) into YDB. PYU, PHY, RHI and FUS cultures are ground up (2-3 5 second bursts in a blender) and all but Pythium and Phytophthora are filtered through a double layer of sterile cheesecloth to remove large mycelial clumps. Ten ml of the culture solutions of *R. solani* and *F. roseum* are added to 90ml of YSB and 10 ml of the *P. capsici* is added to 90 ml of ASB. Two ml of the culture solution of *P. ultimum* is added to 98 ml of ASB. Care must be made not to overinoculate (e.g., solutions should appear fairly clear to the eye, yet when held up to a light a faint cloudiness should be visible) or standards will not behave properly. The inoculum mixtures are placed in microtiter plates using a 12-tipped pipet. 175 μl (single dose) or 100 μl (dose-response test) of inoculum broth is placed in each well of the microtiter plates. The plates with inoculated media are placed in the refrigerator overnight. There are two replications per treatment.

3. Addition of compounds. This operation is carried out in a hood. Six microtiter plates have 245 microliters of sterile water added to their wells ahead of time. 10 Mg a.i. of the compounds are placed in 1 ml 1:1 acetone:methanol. 5 Microliters of this solution is pipetted into the microtiter plates containing the sterile water according to the grid. There are 45 compounds and 3 control treatments per plate. There are 2 replicates per treatment. 25 Microliters of solution is transferred to the inoculated plates with a 96 well replicator. The replicator is flame sterilized with alcohol, rinsed with sterile water, and blotted on sterile paper towels between each transfer.

The results of % control of plant fungi at a certain concentration of some of the compounds of this invention are shown in Table 4.

C. Greenhouse Tests of Plant Disease Control:

Several compounds of this invention were tested for fungicidal activity in vivo against tomato late blight (TLB), wheat powdery mildew (WPM) and wheat leaf rust (WLR) and the results are shown in Table 5. In tests on cereals the plants were trimmed about 24 hours prior to the application of the fungicide compound to provide a uniform plant height and to facilitate uniform application of the compound and inoculation with the fungus. The compounds were dissolved in a 2:1:1 mixture of water, acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

Tomato Late Blight (TLB):

*Phytophthora infestans* was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

Wheat Powdery Mildew (WPM):

*Erysiphe graminis* (f. sp. *tritici*) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

Wheat Leaf Rust (WLR):

*Puccinia recondita* (f. sp. tritici Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultra-low freezer. When stored, spores must be heat shocked for two minutes at 40° F. before use. A spore suspension is prepared from dry uredia by adding 20 mg (9.5 million) per ml of Soltrol oil. The suspension is dispensed into gelatin capsules (0.7 ml capacity) which attach to the oil atomizers. One capsule is used per flat of twenty of the two inch square pots of seven day old Fielder wheat. After waiting for at least 15 minutes for the oil to evaporated from the wheat leaves, the plants are placed in a dark mist chamber (18°-20° C. and 100% relative humidity) for 24 hours. The plants are then put in the greenhouse for the latent period and scored after 10 days for disease levels. Protective and curative tests were inoculated one day after and two days, respectively, before spraying the plants with the test chemicals.

TABLE 3

Biocides Secondary MIC/SOK Test Data (in PPM) for Compounds of Formula I

| Cpd # | SOK | PSFL | PSAE | ECOL | SAUR | ANIG | APUL |
|---|---|---|---|---|---|---|---|
| 1 | >500 | 63 | 125 | 250 | 125 | 16 | 8 |
| 2 | >250 | >250 | >250 | 250 | >250 | >250 | >250 |
| 3 | 250 | 125 | 250 | 250 | 125 | 32 | 250 |
| 4 | 250 | 250 | >250 | >250 | >250 | 63 | 32 |
| 5 | >250 | 16 | 250 | 125 | 16 | 2 | 4 |

TABLE 3-continued

Biocides Secondary MIC/SOK Test Data (in PPM) for Compounds of Formula I

| Cpd # | SOK | PSFL | PSAE | ECOL | SAUR | ANIG | APUL |
|---|---|---|---|---|---|---|---|
| 6 | 125 | 16 | 250 | 250 | 16 | >.13 | 1 |
| 7 | 250 | >250 | >250 | >250 | >250 | >250 | 125 |
| 8 | 250 | 32 | >250 | >250 | >250 | 63 | >250 |
| 9 | 32 | 8 | >250 | >250 | 125 | 8 | 16 |
| 10 | 32 | 16 | >250 | >250 | 125 | 8 | 32 |
| 11 | 32 | 16 | >250 | >250 | 125 | 8 | 32 |
| 12 | 250 | >250 | >250 | >250 | >250 | 8 | 63 |
| 13 | 125 | 32 | >250 | >250 | 63 | 32 | 16 |
| 14 | 125 | >250 | >250 | >250 | >250 | >250 | >250 |
| 15 | >250 | >250 | >250 | >250 | >250 | >250 | 125 |
| 16 | >250 | >250 | >250 | >250 | >250 | >250 | 0.63 |
| 17 | >1000 | >250 | >1000 | >1000 | >1000 | >1000 | >1000 |
| 18 | >250 | >250 | >250 | >250 | >250 | >250 | 63 |
| 19 | >250 | 16 | 63 | 63 | 63 | 4 | 2 |
| 20 | >1000 | >250 | >1000 | >1000 | 1000 | 1000 | 1000 |
| 21 | >250 | >250 | 250 | >250 | >250 | 250 | 250 |
| 22 | >250 | 32 | >125 | 250 | 250 | 63 | 16 |
| 23 | >250 | >250 | >250 | >250 | >250 | 250 | 63 |
| 24 | >250 | >250 | >250 | >250 | >250 | 250 | 125 |
| 25 | >250 | >250 | >250 | >250. | >250 | 250 | 125 |
| 26 | >250 | >250 | >250 | >250 | >250 | 125 | 63 |
| 27 | >250 | >250 | >250 | >250 | >250 | 32 | 63 |
| 28 | 125 | 32 | 32 | 63 | 16 | 16 | 4 |
| 29 | >250 | 250 | >250 | >250 | >250 | >250 | >250 |
| 30 | >250 | 250 | >250 | >250 | >250 | >250 | >250 |
| 31 | 63 | — | 63 | 63 | >250 | 2 | 1 |
| 32 | >250 | — | 32 | >250 | >250 | 63 | 63 |
| 33 | >250 | — | >250 | >250 | 16 | 16 | 8 |

TABLE 3A

Biocides Secondary MIC Test Data (in PPM) for Compounds of Formula I

| Cpd. # | SOK | PSFL | PSAE | ECOL | SAUR | ANIG | APUL |
|---|---|---|---|---|---|---|---|
| 34 | — | — | 500 | >500 | 32 | — | — |
| 35 | — | — | 500 | 16 | 32 | — | — |
| 36 | — | — | 500 | 250 | 63 | — | — |
| 37 | — | — | 250 | 63 | 8 | — | — |
| 38 | — | — | 500 | 250 | 250 | — | — |
| 39 | — | — | 500 | 125 | 16 | — | — |
| 40 | — | — | 125 | 1 | 1 | — | — |
| 41 | — | — | 500 | 250 | 125 | — | — |
| 42 | — | — | 125 | 63 | 16 | — | — |
| 43 | — | — | 500 | 63 | 63 | — | — |
| 44 | — | — | 500 | 63 | 63 | — | — |
| 45 | — | — | >500 | 500 | 250 | — | — |

TABLE 4

In-Vitro Plant Fungicide Test Results for Compounds of Formula I

| Cpd. # | % control at 25 ppm | | | | | | | | |
|---|---|---|---|---|---|---|---|---|---|
| | PYU | PIR | PHY | BOC | HEL | RHI | FUS | SEP | XAN |
| 1 | 100 | 100 | 100 | 100 | 100 | 100 | 100 | 100 | 0 |
| 5 | 100 | 100 | 100 | 100 | 100 | 100 | 100 | 100 | 0 |
| 6 | 100 | 100 | 100 | 100 | 100 | 100 | 100 | 100 | 0 |
| 8 | 100 | 100 | 100 | 100 | 100 | 100 | 100 | 100 | 0 |
| 9 | 0 | 100 | 100 | 100 | 0 | 100 | 0 | 100 | 0 |
| 10 | 100 | 100 | 100 | 100 | 100 | 100 | 100 | 100 | 0 |
| 11 | 100 | 100 | 100 | 100 | 100 | 100 | 100 | 100 | 0 |
| 12 | 0 | 100 | 100 | 0 | 100 | 0 | 0 | 0 | 0 |
| 13 | 100 | 100 | 100 | 100 | 100 | 100 | 100 | 100 | 0 |
| 25 | 100 | 100 | 100 | 100 | 100 | 100 | 100 | 100 | 0 |

TABLE 5

Green House Test Results of Plant Disease Control for Compounds of Formula I

| Comp. # | Rate (ppm) | % Control | | |
|---|---|---|---|---|
| | | TLB | WLR | WPM |
| 8 | 600 | 90 | 75 | 0 |
| 10 | 600 | 75 | 90 | 0 |
| 11 | 600 | 0 | 50 | 0 |
| 12 | 600 | 50 | 90 | 0 |
| 18 | 600 | 75 | 75 | 0 |

TABLE 6

Microorganisms Used in the Biocides Tests

| Name | GRAM | ATCC No. | Abbreviation used |
|---|---|---|---|
| BACTERIA | | | |
| 1. Pseudomonas aeruginosa | (−) | 15442 | PSAE |
| 2. Staphylococcus aureus | (+) | 6538 | SAUR |
| 3. Escherichia coli | (−) | 11229 | ECOL |
| 4. Pseudomonas fluorescens | (−) | 948 | PSFL |
| FUNGI | | | |
| 1. Aspergillus niger | | 6275 | ANIG |
| 2. Aureobasidium pullulans | | 9348 | APUL |

We claim:

1. A process of inhibiting the growth of microbials comprising introducing a microbicidally effective amount of one or more thiocryloyl compounds onto, into, or at a locus subject to microbial attack, said thiocryloyl compounds being of the formula

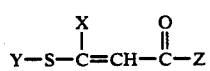

wherein

Z is selected from the group consisting of OR and R;

R is selected from the group consisting of hydrogen; $(C_1-C_{18})$alkyl; $(C_2-C_8)$alkenyl; $(C_2-C_8)$haloalkynyl; 2-(5-chlorothienyl)methyl; phenyl optionally substituted with one or more substituents selected from the group consisting of halo-, $(C_1-C_3)$alkoxy-, nitro-, and $(C_1-C_3)$alkyl; phenacyl optionally substituted with one or more substituents selected from the group consisting of ring halo-,$(C_1-C_3)$alkoxy-, nitro-, and $(C_1-C_3)$alkyl; arylalkyl optionally substituted with one or more substituents selected from the group consisting of ring halo-,$(C_1-C_3)$alkoxy-, nitro-, and $(C_1-C_3)$ alkyl;

X is selected from the group consisting of hydrogen, halogen, phenyl, $CO_2CH_3$, and $(C_1-C_3)$alkyl; and Y is selected from the group consisting of CN, $CH(COCH_3)_2$, $CH_2COCH_3$, $CH_2CN$, $CH_2CO_2C_2H_5$, propargyl, $SCH=CHCO_2CH_3$, $C(=NH)NH_2$ hydrochloride, 2-(5-chlorothienyl)-methyl, and a saturated or unsaturated heterocylic 5- or 6-membered ring with 1 to 4 heteratoms selected from the group consisting of S, O or N, said ring being unsubstituted or substituted with substituents independently selected from the group consisting of unsubstituted or halosubstituted alkyl of 1 to 8 carbon atoms, unsubstituted or halosubstituted alkenyl or alkynyl of 2 to 8 carbon atoms, nitro, cyano, halo, $(C_1-C_8)$alkoxy, amino, alkylamino, dialkyamino, and benzyl; or optionally fused to a benzene ring which is optionally substituted with substituents independently selected from the group consisting of unsubstituted or halosubstituted alkyl of 1 to 8 carbon atoms, unsubstituted or halosubstituted alkenyl or alkynyl of 2 to 8 carbon atoms, nitro, cyano, halo, $(C_1-C_8)$alkoxy, amino, alkylamino, and dialkylamino; or said nitrogens in the nitrogen-containing heterocycles possible being N-oxides;

provided that when Y is heterocyclic, z is $(C_1-C_{18})$alkyl;

provided that when Z is R, X is hydrogen or $(C_1-C_3)$alkyl and Y is CN, R is not substituted or unsubstituted phenyl.

2. The process of claim 1 wherein said compound is selected from the group consisting of
methyl cis-3-thiocyanoacrylate;
cis-3-thiocyanoacrylic acid;
ethyl cis-3-thiocyanoacrylate;
n-butyl cis-3-thiocyanoacrylate;
phenyl cis-3-thiocyanoacrylate;
iodopropargyl cis-3-thiocyanoacrylate;
dimethyl alpha-thiocyanofumarate;
2,5-dinitrobenzyl cis-3-thiocyanoacrylate;
5-chloro-thien-2-yl-methyl cis-3-thiocyanoacrylate;
benzyl cis-3-thiocyanoacrylate;
4-chlorobenzyl cis-3-thiocyanoacrylate;
p-chloroacetophenyl cis-3-thiocyanoacrylate;
3-methoxybenzyl cis-3-thiocyanoacrylate;
2,5-dichlorobenzyl cis-3-thiocyanoacrylate;
cis-beta-carbomethoxyvinylisothiouronium chloride;
methyl cis-3-thio(1-acetylpropan-2-on-1-yl)acrylate;
methyl cis-3-thio(propan-2-on-1-yl)acrylate;
bis-cis-(carbomethoxyvinyl)disulfide;
methyl trans-3-thiocyanoacrylate;
methyl cis-3-propargylthioacrylate;
methyl cis-3-(5-chlorothien-2-yl-methyl)acrylate;
methyl 3-bromo-3-thiocyanoacrylate;
cis-4-thiocyano-3-buten-2-one;
methyl cis-3-(cyanomethylthio)acrylate;
methyl cis-3-(ethylcarboxymethylthio)acrylate;
cis-5-thiocyano-4-penten-3-one;
cis-8-thiocyano-7-octen-6-one;
4-phenyl-4-thiocyano-3-buten-2-one;
4-(2-mercaptobenzothiazolyl)-3-buten-2-one;
cis-4-(5-mercapto-1-methyltetrazolyl)-3-buten-2-one;
cis-4-(2-mercaptothiazolinyl)-3-buten-2-one;
trans-4-(2-mercaptothiazolinyl)-3-buten-2-one;
cis-4-(2-mercaptopyridinyl)-3-buten-2-one;
trans-4-(2-mercaptopyridinyl)-3-buten-2-one;
cis-4-(2-mercaptopyridinyl-N-oxide)-3-buten-2-one;
cis-4-(2-mercaptothiazolyl)-3-buten-2-one;
trans-4-(2-mercaptothiazolyl)-3-buten-2-one;
1-mercaptoimidazolyl-3-buten-2-one;
cis-4-(2-mercapto-1-methylimidazolyl)-3-buten-2-one; and
4-(2-mercapto-1-methylimidazolyl)-3-buten-2-one.

3. A process comprising according to claim 1 wherein said locus is selected from the group consisting of wood, paint, adhesive, glue, paper, pulp/paper slurries, textile, leather, plastics, cardboard, lubricants, cosmetics, food, caulking, feed, and industrial cooling water from microorganisms.

4. The process of claim 3 wherein the compound is selected from the group consisting of methyl cis-3-thiocyanoacrylate, iodopropargyl cis-3-thiocyanoacrylate, methyl trans-3-thiocyanoacrylate, and cis-4-thiocyano-3-buten-2-one.

5. The process of claim 4 wherein said is selected from the group consisting of pulp/paper slurries and industrial cooling water.

6. The process of claim 3 wherein the amount of said compound is about 5 to about 300 ppm based on weight of said locus.

* * * * *